US00PP26604P3

(12) United States Plant Patent
Trees

(10) Patent No.: US PP26,604 P3
(45) Date of Patent: Apr. 12, 2016

(54) ***ERYSIMUM* PLANT NAMED 'BALCHERMAUV'**

(50) Latin Name: *Erysimum linifolium*
Varietal Denomination: Balchermauv

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 120 days.

(21) Appl. No.: 14/121,131

(22) Filed: Aug. 4, 2014

(65) Prior Publication Data
US 2016/0037696 P1 Feb. 4, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Audrey Charles

(57) ABSTRACT

A new and distinct cultivar of *Erysimum* plant named 'Balchermauv', characterized by its medium lavender-colored flowers, medium green-colored foliage, and moderately vigorous, mounded-upright growth habit, is disclosed.

1 Drawing Sheet

Latin name of genus and species of plant claimed: *Erysimum linifolium.*

Variety denomination: 'Balchermauv'.

BACKGROUND OF THE INVENTION

The present invention relates to a new and distinct cultivar of *Erysimum* plant botanically known as *Erysimum linifolium* and hereinafter referred to by the cultivar name 'Balchermauv'.

The new cultivar originated in a controlled breeding program in Guadalupe, Calif. during the summer of 2010. The objective of the breeding program was the development of *Erysimum* cultivars having rich-colored inflorescences and well-branched growth habits.

The new *Erysimum* cultivar is the result of open-pollination. The female (seed) parent of the new cultivar is 'Bowles' Mauve', not patented, characterized by its medium lavender-colored flowers, grey-green colored foliage, and moderately vigorous, mounded growth habit. The male (pollen) parent of the new cultivar is unknown. The new cultivar was discovered and selected as a single flowering plant within the progeny of the above stated open-pollination during September 2011 in a controlled environment in Guadalupe, Calif.

Asexual reproduction of the new cultivar by terminal stem cuttings since September 2011 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balchermauv' as a new and distinct cultivar of *Erysimum* plant:

1. Medium lavender-colored flowers;
2. Medium green-colored foliage; and
3. Moderately vigorous, mounded-upright growth habit.

Of the many commercially available *Erysimum* cultivars, the most similar in comparison to the new cultivar is the female parent 'Bowles' Mauve', not patented. However, in side by side comparisons, plants of the new cultivar differ from plants of 'Bowles' Mauve' in at least the following characteristics:

1. Plants of the new cultivar are better branched than plants of 'Bowles' Mauve'; and
2. Plants of the new cultivar have darker colored foliage than plants of 'Bowles' Mauve'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balchermauv'. The plants were grown in one-gallon containers for approximately two months in a greenhouse and one month outdoors in Elburn, Ill. Plants were given one pinch prior to transplant and one pinch two weeks after transplant.

DETAILED BOTANICAL DESCRIPTION

Figure 1:
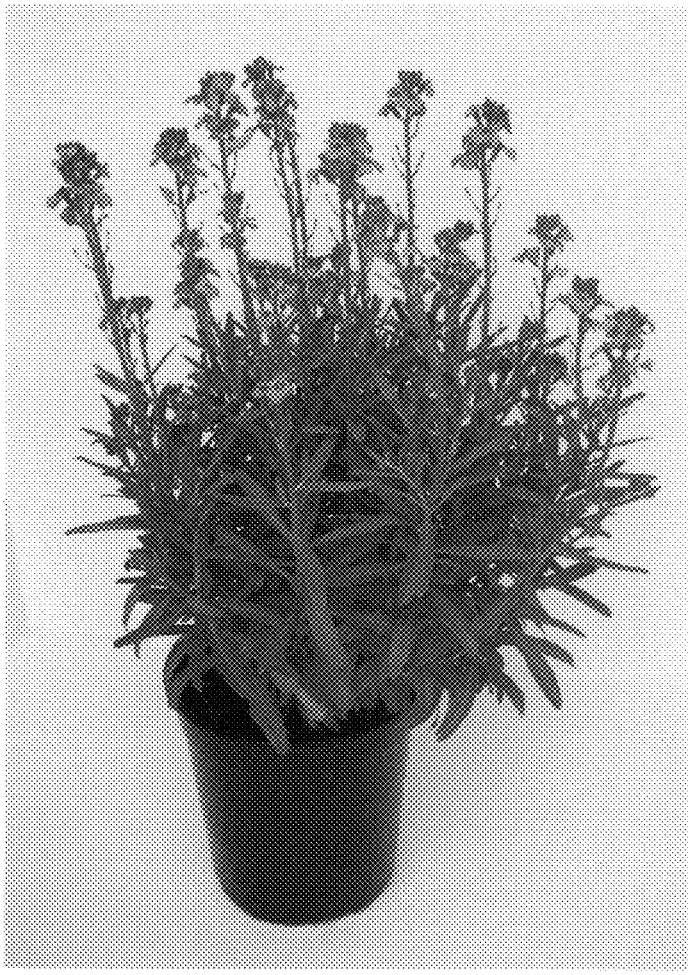
FIG. 1 illustrates a side view of the overall growth and flowering habit of 'Balchermauv'.
Figure 2:
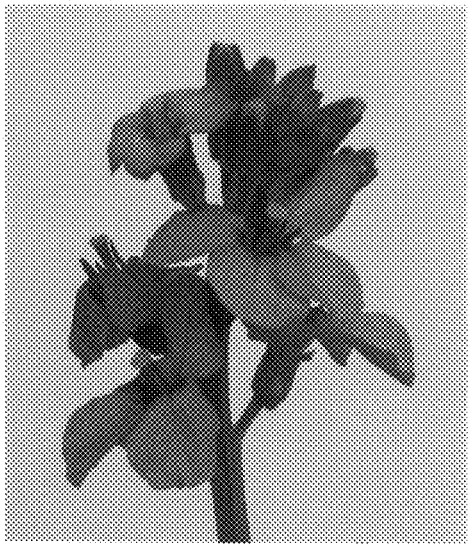
FIG. 2 illustrates a close-up view of an individual inflorescence of 'Balchermauv'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in West Chicago, Ill.

The following descriptions and measurements describe plants produced from cuttings from stock plants and grown under conditions comparable to those used in commercial practice. The plants were grown utilizing a soilless growth medium in one-gallon containers for approximately two months in a greenhouse and one month outdoors in Elburn, Ill. Plants were given one pinch prior to transplant and one pinch two weeks after transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Erysimum linifolium* cultivar Balchermauv.

Parentage:

*Female parent*.—'Bowles' Mauve', not patented.

*Male parent*.—Unknown.

Propagation:

*Type cutting*.—Terminal stem.

*Time to initiate roots*.—Approximately 10 to 12 days.

*Time to produce a rooted cutting*.—Approximately 35 to 42 days.

*Root description*.—Fine, fibrous.

*Rooting habit*.—Freely branching.

Plant description:

*Commercial crop time*.—Approximately 10 to 12 weeks from a rooted cutting to finish in a 15 cm pot.

*Growth habit and general appearance*.—Moderately vigorous, mounded-upright.

*Size*.—Height from soil level to top of plant plane: Approximately 42.0 cm. Width: Approximately 31.0 cm.

*Branching habit*.—Freely branching. Quantity of main branches per plant: Approximately 7.

*Branch*.—Shape: Ribbed. Strength: Strong. Length to base of inflorescence: Approximately 13.0 cm. Diameter: Approximately 5.0 mm. Length of central internode: Approximately 7.0 mm. Texture: Densely pubescent with appressed hairs. Color of young and mature stems: 145A.

Foliage description:

*General description*.—Quantity of leaves per main branch: Approximately 15. Fragrance: None. Form: Simple. Arrangement: Alternate in a spiral.

*Leaves*.—Aspect: Perpendicular or obtuse angle to stem. Shape: Oblanceolate. Margin: Entire. Apex: Acute. Base: Attenuate, sessile. Venation pattern: Pinnate. Length of mature leaf: Approximately 7.0 cm. Width of mature leaf: Approximately 1.3 cm. Texture of upper and lower surfaces: Densely pubescent with appressed hairs. Color of upper surface of young and mature foliage: Closest to N137B with midvein of 147D, other venation indistinguishable. Color of lower surface of young and mature foliage: 137B with midvein of 147C, other venation indistinguishable.

Flowering description:

*Flowering habit*.—'Balchermauv' is freely flowering under outdoor growing conditions with substantially continuous blooming from early spring through autumn.

*Lastingness of individual flower on the plant*.—Approximately 6 to 8 days.

Inflorescence description:

*General description*.—Type: Terminal raceme. Quantity per plant: Approximately 27. Fragrance: Slight, sweet. Length or height: Approximately 17.0 cm. Width: Approximately 3.0 cm. Quantity of fully open flowers per inflorescence: Approximately 5.

Flower description:

*Type*.—Solitary, self-cleaning.

*Bud*.—Rate of opening: Generally takes 4 to 5 days for bud to progress from first color to fully open flower.

*Bud just before opening*.—Shape: Ovoid and slightly flattened. Length: Approximately 9.0 mm. Diameter: Approximately 5.0 mm. Color: Calyx of 145A with an overlay of N186A at tips; petals of 79C.

*Corolla*.—Shape: Lobes cruciform with claws surrounded by calyx. Aspect: Facing upward and outward. Diameter: Approximately 2.0 cm. Depth: Approximately 1.1 cm.

*Petals*.—Quantity: 4. Shape: Obovate. Margin: Entire, undulate. Apex: Obtuse. Base: Attenuate. Length of lobes: Approximately 9.0 mm. Width of lobes: Approximately 1.0 cm. Length of claws: Approximately 7.0 mm. Width of claws: Approximately 1.0 mm. Color of upper surface of lobes when first open: N82D with venation of N82C. Color of lower surface of lobes when first open: NN155D with an overlay of N82D at apex. Color of upper surface of lobes when fully open: N82B with venation of N82A. Color of lower surface of lobes when fully open: N82C with venation of N82B. Color of upper and lower surfaces of claws: NN155A with a midvein of 145A.

*Calyx*.—Shape: Cupped. Diameter: Approximately 5.0 mm.

*Sepals*.—Quantity per flower: 4, distinct. Shape: Lanceolate. Apex: Acute. Base: Truncate. Length: Approximately 8.0 mm. Width: Approximately 2.5 mm. Texture of inner surface: Glabrous. Texture of outer surface: Densely pubescent with appressed hairs. Color of inner surface: 138C. Color of outer surface: 138A with an overlay of 187A and N186A.

*Pedicel*.—Strength: Strong. Aspect: Acute angle to stem. Length: Approximately 5.0 mm. Diameter: Approximately 1.0 mm. Texture: Densely pubescent with appressed hairs. Color: 137C.

*Reproductive organs*.—Androecium: Stamen quantity: 6 per flower. Stamen length: Approximately 9.0 mm, 1 pair slightly shorter and inserted lower. Filament texture: Glabrous. Filament color: 145C. Anther shape: Sagittate, dorsifixed. Anther length: Approximately 2.0 mm. Anther color: 151 D, darkening to N92A with age. Pollen amount: Sparse. Pollen color: 1D. Gynoecium: Pistil quantity: 1 per flower. Pistil length: Approximately 1.0 cm. Stigma shape: Bifid. Stigma length: Approximately 1.0 mm. Stigma color: 151 D. Style length: Approximately 1.0 mm. Style color: 144A. Ovary length: Approximately 8.0 mm. Ovary diameter: Approximately 1.5 mm. Ovary texture: Densely pubescent with appressed hairs. Ovary color: 144A, appears lighter colored due to pubescence.

Seed and fruit production: Neither seed nor fruit production has been observed.

Disease and pest resistance: Resistance to pathogens and pests common to *Erysimum* has not been observed.

What is claimed is:

1. A new and distinct cultivar of *Erysimum* plant named 'Balchermauv' substantially as herein shown and described.

* * * * *